United States Patent
Fried et al.

(10) Patent No.: US 11,944,833 B2
(45) Date of Patent: Apr. 2, 2024

(54) USER CENTERED SYSTEM FOR RECHARGING IMPLANTED NEUROSTIMULATOR

(71) Applicant: Medtronic, Inc., Minneapolis, MN (US)

(72) Inventors: Andrew Fried, Woodbury, MN (US); Janet Creaser, New Brighton, MN (US); Prathyusha Marri, Blaine, MN (US); Charles Nowell, Longwood, FL (US); Robert Schulzetenberg, Columbia Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 60 days.

(21) Appl. No.: 17/078,507

(22) Filed: Oct. 23, 2020

(65) Prior Publication Data
US 2021/0121708 A1    Apr. 29, 2021

Related U.S. Application Data

(60) Provisional application No. 62/926,136, filed on Oct. 25, 2019.

(51) Int. Cl.
*A61N 1/00* (2006.01)
*A61N 1/08* (2006.01)
*A61N 1/36* (2006.01)
*A61N 1/372* (2006.01)
*A61N 1/378* (2006.01)

(52) U.S. Cl.
CPC .............. *A61N 1/3787* (2013.01); *A61N 1/08* (2013.01); *A61N 1/36128* (2013.01); *A61N 1/37247* (2013.01)

(58) Field of Classification Search
CPC ........ A61N 1/3787; A61N 1/378; A61N 1/08; A61N 1/36128; A61N 1/37247; A61N 1/37252
See application file for complete search history.

(56) References Cited

U.S. PATENT DOCUMENTS

| | | | |
|---|---|---|---|
| 8,265,556 | B2 | 9/2012 | Tekin et al. |
| 8,346,361 | B2 | 1/2013 | Bauhahn et al. |
| 9,142,989 | B2 | 9/2015 | Fell et al. |
| 9,707,402 | B2 | 7/2017 | Aghassian |

(Continued)

FOREIGN PATENT DOCUMENTS

WO    WO2010042056 A1    4/2010

*Primary Examiner* — Scott M. Getzow
(74) *Attorney, Agent, or Firm* — Husch Blackwell LLP

(57) ABSTRACT

Systems and methods for improved user experience with rechargers for implantable medical devices. An external charging device for providing power to a rechargeable implantable device can determine a firmware state of the external charging device during recharging of the rechargeable implantable device, display a searching indication using a light indicator when the firmware state is determined to be in a searching state, display a charging indication using the light indicator when the firmware state is determined to be a charging state, and display an error indication using the light indicator when the firmware state is determined to be an error state. An optional user device application can provide complementary graphical user interfaces according to the firmware states.

17 Claims, 19 Drawing Sheets

(56) References Cited

U.S. PATENT DOCUMENTS

| | | |
|---|---|---|
| 10,105,545 B2 | 10/2018 | Aghassian |
| 10,226,637 B2 | 3/2019 | Aghassian et al. |
| 10,468,903 B2 | 11/2019 | Park et al. |
| 10,682,521 B2* | 6/2020 | Jiang .................... A61N 1/3787 |
| 10,722,721 B2 | 7/2020 | Nassif et al. |
| 2009/0259273 A1* | 10/2009 | Figueiredo ......... A61N 1/37252 |
| | | 607/32 |
| 2014/0074185 A1* | 3/2014 | Fell ........................ H02J 50/80 |
| | | 320/108 |
| 2018/0110973 A1* | 4/2018 | Johnson ................ A61B 5/4836 |
| 2018/0345025 A1* | 12/2018 | Stinauer .............. H01F 27/2876 |
| 2019/0344087 A1 | 11/2019 | Ter-Petrosyan et al. |
| 2020/0230427 A1 | 7/2020 | Nassif et al. |

* cited by examiner

| Tone | Light | Meaning |
|---|---|---|
| Repeating beeping tone | Spinning | Recharger is searching for the neurostimulator. |
| 2 tones, rising in pitch | Solid | Neurostimulator has been found. |
| None | Slow Pulsing | Recharging neurostimulator. |
| A series of tones, rising in pitch | Solid | Recharging session is complete. |
| 2 tones, falling in pitch and repeating | Flashing | Alert/error |

FIG. 3B

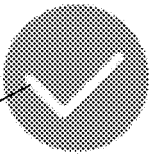

| Image on the app | What to do |
|---|---|
| The connection icon <br> 550 | Keep the recharger in place until you see the neurostimulator battery icon: |
| OR | |
| A row of 3 numbers <br> 556  558 <br> 44  49  52 <br> Low  High <br> 554 <br> 552 <br> Note: Numbers shown are only examples. | 1. Move the recharger until the value of the middle number is close to the value of the number on the right (the High number). <br><br> 2. Keep the recharger in place until you see the neurostimulator battery icon: |

Good

562

USER CENTERED SYSTEM FOR RECHARGING IMPLANTED NEUROSTIMULATOR

CROSS-REFERENCE TO RELATED APPLICATIONS

This application claims the benefit of U.S. Provisional Application No. 62/926,136 filed on Oct. 25, 2019, the entirety of which is incorporated herein by reference.

FIELD

The present technology is generally related to medical devices, and more particularly, to user-facing interfaces for medical devices.

BACKGROUND

The medical device industry produces a wide variety of electronic and mechanical devices for treating patient medical conditions. Depending upon medical condition, medical devices can be surgically implanted or connected externally to the patient receiving treatment. Clinicians use medical devices alone or in combination with drug therapies and surgery to treat patient medical conditions. For some medical conditions, medical devices provide the best, and sometimes the only, therapy to restore an individual to a more healthful condition and a fuller life. Examples of implantable medical devices include neuro stimulators, drug delivery pumps, pacemakers, defibrillators, diagnostic recorders, and cochlear implants. Some implantable medical devices provide therapies with significant power demands. To reduce the size of the power source and to extend the life of the power source, some of these implantable devices can be recharged while implanted with a transcutaneous recharge signal produced by one or more field-producing coils external to the patient.

Implantable medical devices configured for recharging are typically configured with either the recharging coil internal to the medical device housing, external to the housing, or remotely located away from the housing. Charging an implantable medical device can be a time-intensive burden to patients and is often the primary area of complaints among traditional implantable and rechargeable medical devices. Further, some patients often have cognitive impairment, mobility, or motor function issues that can exacerbate these problems.

A main area of complaint is not being able to easily achieve coupling of the recharger to the implantable medical device, or not being able to achieve a high quality coupling. This can lead patients to be hyper vigilant about watching their devices to ensure a coupling and/or a high quality coupling. Additionally, users are often required to establish and maintain coupling between their external charging device and the implanted device for hours at a time, sometimes as often as every day or multiple times per day.

Therefore, there is a need for a recharger for implantable medical devices with an improved user experience.

SUMMARY

The techniques of this disclosure generally relate to improvements in the user experience for rechargers of implantable devices. More particularly, embodiments provide simple and comprehensive user interfaces that reduce the overall burden and improve the usability of systems relative to implantable devices.

In one aspect, the present disclosure provides an external charging device for providing power to a rechargeable implantable device, the external charging device comprising: a housing; a single button arranged in the housing; an indicator light illuminating the single button, the indicator light comprising at least one light emitting diode (LED); at least one processor and a memory operably coupled to the at least one processor; and instructions that, when executed on the at least one processor, cause the at least one processor to: determine a firmware state of the external charging device during recharging of the rechargeable implantable device, display a searching indication using the indicator light when the firmware state is determined to be in a searching state, display a charging indication using the indicator light when the firmware state is determined to be a charging state, and display an error indication using the indicator light when the firmware state is determined to be an error state.

In another aspect, the disclosure provides a system for medical treatment, the system comprising: a rechargeable implantable medical device configured to provide a medical therapy to a patient; and a recharger including an indicator light having a at least one light emitting diode (LED) illuminating a single button, at least one processor and a memory operably coupled to the at least one processor; and instructions that, when executed on the at least one processor, cause the at least one processor to implement: a user interface engine configured to determine a firmware state of the external charging device during recharging of the rechargeable implantable device, and display status of the recharging on the indicator light based on the determined firmware state.

In an embodiment, the system can further comprise a mobile user device including computing hardware of at least one processor and memory operably coupled to the at least one processor; and instructions that, when executed on the mobile user device, cause the mobile user device to implement: an input/output engine operably coupled to the recharger and configured to transmit data to and receive data from the recharger; a graphical user interface engine configured to display interfaces according to a state machine including: a graphical indication of charging when the recharger is actively charging the rechargeable implantable medical device, a graphical indication of searching when the recharger is actively searching for the rechargeable implantable medical device, and a graphical indication of an error when the recharger cannot charge or find the rechargeable implantable medical device.

In another aspect, the disclosure provides a method for commanding a first hardware device for specialized programming with a second hardware device, the second hardware device having a single binary actuator, the method comprising: operably coupling the second hardware device to a power source; activating the single binary actuator for a first duration; activating the single binary actuator for a second duration; activating the single binary actuator for a third duration; uncoupling the second hardware device from the power source; and transmitting a specialized programming command from the second hardware device to the first hardware device.

In embodiments, the first hardware device can comprise an implanted neurostimulator. In embodiments, the second hardware device can comprise an external charging device. In embodiments, the single binary switch can comprise a button.

In a feature and advantage of embodiments, a complex internal workflow of a recharger is reduced to a simple mental model for patients. For example, states that are typically divided with respect to the charging device operation can be combined so that the user is presented fewer and thus, more manageable, states.

In another feature and advantage of embodiments, user interfaces can hide behavior that is not important to the user, such as open loop vs. closed loop charging, temperature limiting, constant-voltage charging, etc.

In another feature and advantage of embodiments, a recharger can have a single button capable of displaying multiple states to the user. For example, the button can be a translucent "power" button with a plurality of light-emitting diodes (LEDs) arranged in a ring underneath the button. A single well-understood button is highly desirable for a number of reasons. For example, devices having buttons and icons unknown to the user have a high learning curve to use. Moreover, devices having multiple buttons can likewise be difficult to use. Further, devices having too many LEDs or devices with a backlit screen can use too much energy. Thus, the single well-understood button having an energy-conserving number of LEDs provides a desirable simplified user interface.

In another feature and advantage of embodiments, a clinician-mode can be commanded in a medical device having only a single button. For example, clinician-only feature(s) can be accessed using a recharger. Clinician-only features can be initiated when the recharger is connected to a charging dock (or external power supply) and with a single button. In an embodiment, a multiple-press sequence initiates the clinician-only access. In contrast to devices having multiple buttons in which a special sequence can be easily implemented by presses of the various buttons such that the multiple buttons are the key variables, the sequence for a single button does not have that luxury and thus takes an additional variable—time—into consideration.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 3B is a table of user interface indications for the state machine of FIG. 3A, according to an embodiment.

FIG. 5G is an annotated table of graphical user interfaces and user instructions for a client device, according to an embodiment.

DETAILED DESCRIPTION

Figure 1:
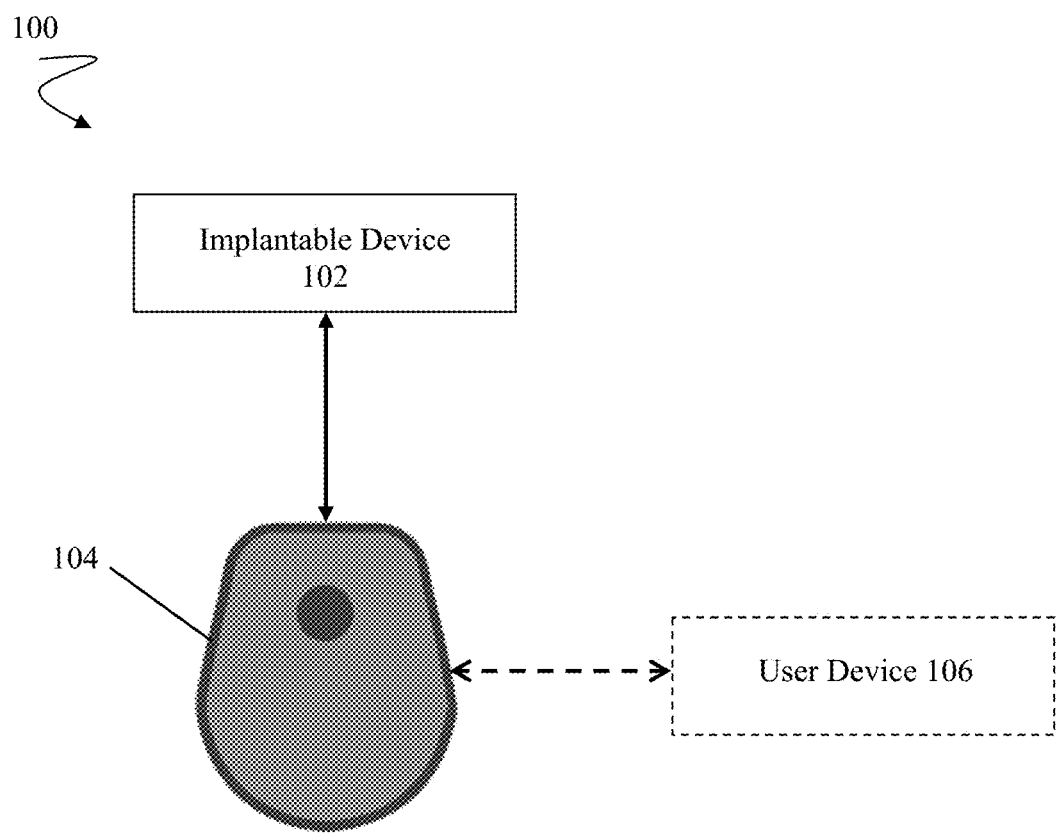
FIG. 1 is a block diagram of a system for recharging an implantable medical device, according to an embodiment.

Referring to FIG. 1, a block diagram of a system 100 for recharging an implantable medical device is depicted, according to an embodiment. System 100 generally comprises an implantable medical device 102, a recharger 104, and optionally, a user device 106.

Implantable medical device 102 comprises any medical device that can be surgically implanted or connected externally to the patient to treat patient medical conditions. In an embodiment, implantable medical device 102 can include implantable neuro stimulators (INS), drug delivery pumps, pacemakers, defibrillators, diagnostic recorders, or cochlear implants. In an embodiment, implantable medical device 102 can include a battery that requires periodic charging or replenishing.

Recharger 104 is configured to replenish power in rechargeable implantable medical devices, such as implantable medical device 102. In embodiments, recharger 104 itself includes a battery that can be operably coupled to implantable medical device 102 to replenish the battery of implantable medical device 102. Accordingly, recharger 104 can itself be charged to replenish the battery of recharger 104, such as to an external power supply or dock.

In embodiments, patients are the primary users of the recharger 104 and coordinate recharging of implantable medical device 102 with recharger 104. In an embodiment, clinicians are further able to interface with recharger 104 to coordinate or alter recharging of implantable medical device 102. In embodiments, clinicians can update certain settings (such as volume of recharger 104 and recharger 104 speed/mode).

Optional user device 106 comprises a mobile platform such as a phone or tablet configured to run specialized software. For example, recharge application software can be hosted on user device 106. Recharge application software is an application configured to communicate with recharger 104. Recharge application software can supplement the user experience of recharger 104.

Figure 2:
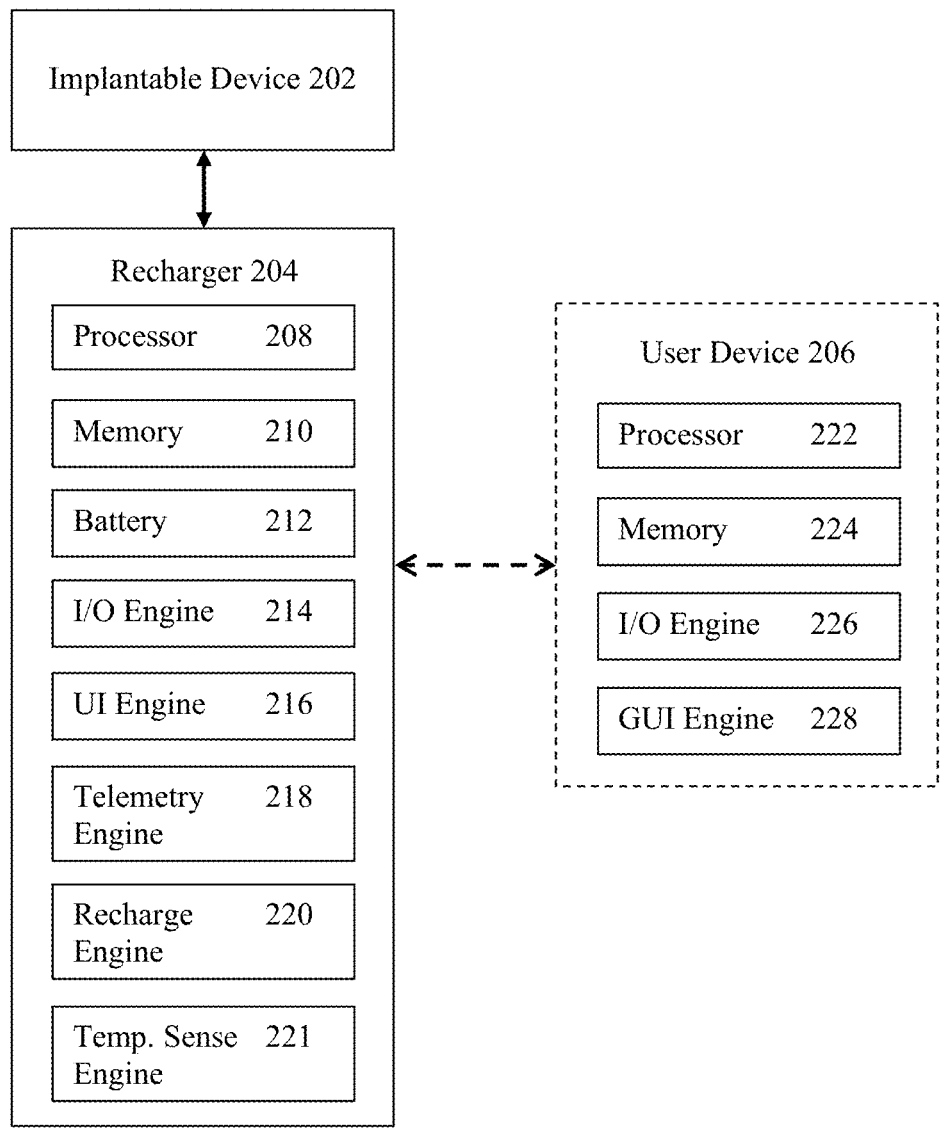
FIG. 2 is a further block diagram of the system for recharging an implantable medical device of FIG. 1, according to an embodiment.

Referring to FIG. 2, a further block diagram of system 100 for recharging an implantable medical device of FIG. 1 is depicted, according to an embodiment. For ease of explanation, FIG. 2 is labeled as system 200 with corresponding element numbers. However, one skilled in the art will readily appreciate that the components of system 100 can be implemented as part of system 200.

System 200 generally comprises an implantable medical device 202, a recharger 204, and an optional user device 206. Implantable medical device 202 can be substantially similar to implantable medical device 102. Recharger 204 can be substantially similar to recharger 104. Optional user device 206 can be substantially similar to optional user device 106.

In an embodiment, implantable medical device 202 can comprise a processor, a memory, a battery, a stimulation engine, a telemetry engine, a recharge engine, a temperature sensing engine, a charge sensor engine (for current, voltage), etc. for providing therapy to a patient. Such components are not depicted in FIG. 2 for ease of explanation. One skilled in the art will readily appreciate that implantable medical device can comprise corresponding components that communicate with the various components of recharger 204 as described herein.

Some of the subsystems of system 200 include various engines or tools, each of which is constructed, programmed, configured, or otherwise adapted, to autonomously carry out a function or set of functions. The term engine as used herein is defined as a real-world device, component, or arrangement of components implemented using hardware, such as by an application specific integrated circuit (ASIC) or field-programmable gate array (FPGA), for example, or as a combination of hardware and software, such as by a microprocessor system and a set of program instructions that adapt the engine to implement the particular functionality, which (while being executed) transform the microprocessor system into a special-purpose device. An engine can also be implemented as a combination of the two, with certain functions facilitated by hardware alone, and other functions facilitated by a combination of hardware and software. In certain implementations, at least a portion, and in some cases, all, of an engine can be executed on the processor(s) of one or more computing platforms that are made up of hardware (e.g., one or more processors, data storage devices such as memory or drive storage, input/output facilities such as network interface devices, video devices, keyboard, mouse or touchscreen devices, etc.) that execute an operating system, system programs, and application programs, while also implementing the engine using multitasking, multithreading, distributed (e.g., cluster, peer-peer, cloud, etc.) processing where appropriate, or other such techniques. Accordingly, each engine can be realized in a variety of physically realizable configurations, and should generally not be limited to any particular implementation exemplified herein, unless such limitations are expressly called out. In addition, an engine can itself be composed of more than one sub-engines, each of which can be regarded as an engine in its own right. Moreover, in the embodiments described herein, each of the various engines corresponds to a defined autonomous functionality; however, it should be understood that in other contemplated embodiments, each functionality can be distributed to more than one engine. Likewise, in other contemplated embodiments, multiple defined functionalities may be implemented by a single engine that performs those multiple functions, possibly alongside other functions, or distributed differently among a set of engines than specifically illustrated in the examples herein.

Recharger 204 is configured to control all aspects of a recharge session. In an embodiment, recharger 204 comprises a processor 208, a memory 210, a battery 212, an input/output (I/O) engine 214, a user interface (UI) engine 216, and telemetry engine 218, recharge engine 220, and temperature sense engine 221. Accordingly, separate user device 206 is not required for recharging functionality.

Processor 208 can be any programmable device that accepts digital data as input, is configured to process the input according to instructions or algorithms, and provides results as outputs. In an embodiment, processor 208 can be a central processing unit (CPU) configured to carry out the instructions of a computer program. Processor 208 is therefore configured to perform at least basic arithmetical, logical, and input/output operations. As depicted, processor 208 is specialized for recharger 204 operation.

Memory 210 can comprise volatile or non-volatile memory as required by the coupled processor 208 to not only provide space to execute the instructions or algorithms, but to provide the space to store the instructions themselves. In embodiments, volatile memory can include random access memory (RAM), dynamic random access memory (DRAM), or static random access memory (SRAM), for example. In embodiments, non-volatile memory can include read-only memory, flash memory, ferroelectric RAM, hard disk, floppy disk, magnetic tape, or optical disc storage, for example. The foregoing lists in no way limit the type of memory that can be used, as these embodiments are given only by way of example and are not intended to limit the scope of embodiments.

Battery 212 comprises one or more electrochemical cells to power recharger 204. Further, battery 212 can be configured to transfer or otherwise replenish power to the battery of implantable device 202 when recharger 204 is operably coupled to implantable device 202.

I/O engine 214 is configured to communicate with user device 206. In an embodiment, I/O engine 214 is configured for radio, free-space optical, sonic, or electromagnetic induction communication, such as BLUETOOTH, WIFI, or RFID. In embodiments, recharger 204 can comprise networking hardware. I/O engine 214 is configured to operate the networking hardware to transmit and receive network communications.

UI engine 216 is configured to present indications related to recharger 204 to a user. In embodiments, the user can be a patient of implantable device 202, or a clinician administering implantable device 202. For example, UI engine 216 can receive commands from a firmware state machine (such as that in recharge engine 220) to change indications on the UI. Accordingly, user interface states corresponding to the firmware state are changed. In some embodiments, the UI engine can receive as input the command to start or stop the UI indication when the recharger 204 changes states. Accordingly, firmware states are aggregated or grouped into user interface states. Grouping of complex firmware states simplifies the user experience for the user.

In an embodiment, recharger 204 comprises one or more light indicators. Accordingly, UI engine 216 comprises instructions to operate the indicators. For example, recharger 204 can include a single "button" configured with a plurality of LEDs illuminating the single button, and three indicators configured with a plurality of LEDs depicting a "battery," as will be described with respect to FIG. 8A. For example, the single button can start or stop a recharging session and change states of recharger 204. In an embodiment, the single button has a depressed mechanical design in order to prevent unintended button presses.

In an embodiment, UI engine 216 can use different colored LEDs, such as green and orange. In an embodiment, recharger 204 further comprises a speaker. Accordingly, UI engine 216 comprises instructions to operate the speaker, such as with beeps or tones. Because the visual interface of recharger 204 can be hidden or difficult to see by a user operating the recharger when recharger 204 is coupled to the patient, supplemental audio indication is desirable.

During an INS Recharge Session, visual feedback can include an indication of Searching for INS, INS Coupling Interrupted, INS Charge Complete, Alert, and Error.

UI engine 216 can further accept input from the user to start a recharge session, change state (example: going to off or idle), arm the recharger for Physician Mode Recharge, power reset the recharger (such as holding for at least 20-30 seconds).

For patients with components or devices that have a maximum service life, UI engine 216 is further configured to detect maximum service life and output an additional tone to indicate that a component or device has reached elective replacement. Many patients only use a charger, such as recharger 204, and not the programmer (i.e. particular software on optional user device 206), because the patient's therapy settings never need to be changed. Thus, having a maximum service life indication provides a higher probability that the user will hear the indication. In embodiments, the additional tone is placed at the beginning of recharge so as to not annoy the user.

Telemetry engine 218 is configured to communicate with implantable device 202. For example, data from implantable device 202 can be acquired via telemetry engine 218, which facilitates communication between the recharger 204 and the implantable device 202. In embodiments, telemetry engine 218 can include an antenna configured to emit the recharging field, or in other embodiments, two separate antennae can be used, one for communication and the other for the recharging field. In some embodiments, telemetry engine 218 can be configured to communicate with implantable device 202 on regular intervals to obtain sensory information from the implant, such as temperature, charge current, charge voltage, etc. In some embodiments, the telemetry engine can be configured to change durations between telemetry events with recharger 204 and implantable device 202. Doing so enables recharger 204 to provide more timely feedback to the user in situations where the user is actively searching for the implant (either initially or when coupling has been lost).

Recharge engine 220 can comprise a primary coil and drive circuitry configured to supply recharging power to implantable device 202. In an embodiment, recharge engine 220 can further include one or more sensors to detect the relative presence of implantable device 202. In an embodiment, one or more sensors are configured to detect an implantable neurostimulator (INS) via metal detection as part of a location function. For example, one or more sensors can detect a relative degree of metal loading (high loading meaning the device is proximal the sensor; low loading meaning the device is distal the sensor). In embodiments, one or more sensors can detect a reflected impedance of the INS.

In embodiments, telemetry engine 218 and recharge engine are both are controlled by separate microprocessors and activate separate coils for inductive telemetry (shown in FIG. 2 as a single processor for ease of explanation). In another embodiment, telemetry engine 218 can interface with an RF antenna and communicate at higher frequencies (MICS band or BLE).

Temperature sense engine 221 is configured with one or more temperature sensors and configured to determine a temperature of recharger 204.

Optional user device 206 comprises a processor 222, a memory 224, an I/O engine 226, and a graphical user interface (GUI) engine 228.

Processor 222 and memory 224 can be similar to processor 208 and memory 210 described above.

I/O engine 226 is configured to communicate with recharger 204. In an embodiment, I/O engine 226 is configured for radio, free-space optical, sonic, or electromagnetic induction communication, such as BLUETOOTH, WIFI, or RFID. In embodiments, user device 206 can comprise networking hardware. I/O engine 226 is configured to operate the networking hardware to transmit and receive network communications, including to other networked devices (not shown).

GUI engine 228 is configured to present graphical user indications related to recharger 204 to a user. Accordingly, GUI engine 228 is further configured to determine a state of recharger 204 to identify appropriate information to display to the user. In embodiments, the user can be a patient of implantable device 202, or a clinician administering implantable device 202.

For example, GUI engine 228 can comprise mobile platform application software. The mobile platform application can be configured to provide more detailed, supplemental recharge information compared to recharger 204 and UI engine 216. Effectively, GUI engine 228 provides a dashboard of what recharger 204 is doing.

In an embodiment, the mobile platform application can be configured to accept input from the user that translates into input commands that are provided to recharger 204. These commands can include inputs from a patient or clinician, such as open/close recharge application, view recharge application version information, update recharge application, select recharge mode, adjust volume, and access diagnostics data.

As described herein, recharger 204 is configured to operate independently to control all aspects of a recharge session. In embodiments, user device 206 operates dependent on recharger 204. Accordingly, to complement the hardware UI of UI engine 216 of light and sound indications, user device 206 via GUI engine 228 can display further information in a graphical form about the session and device.

Figure 3A:
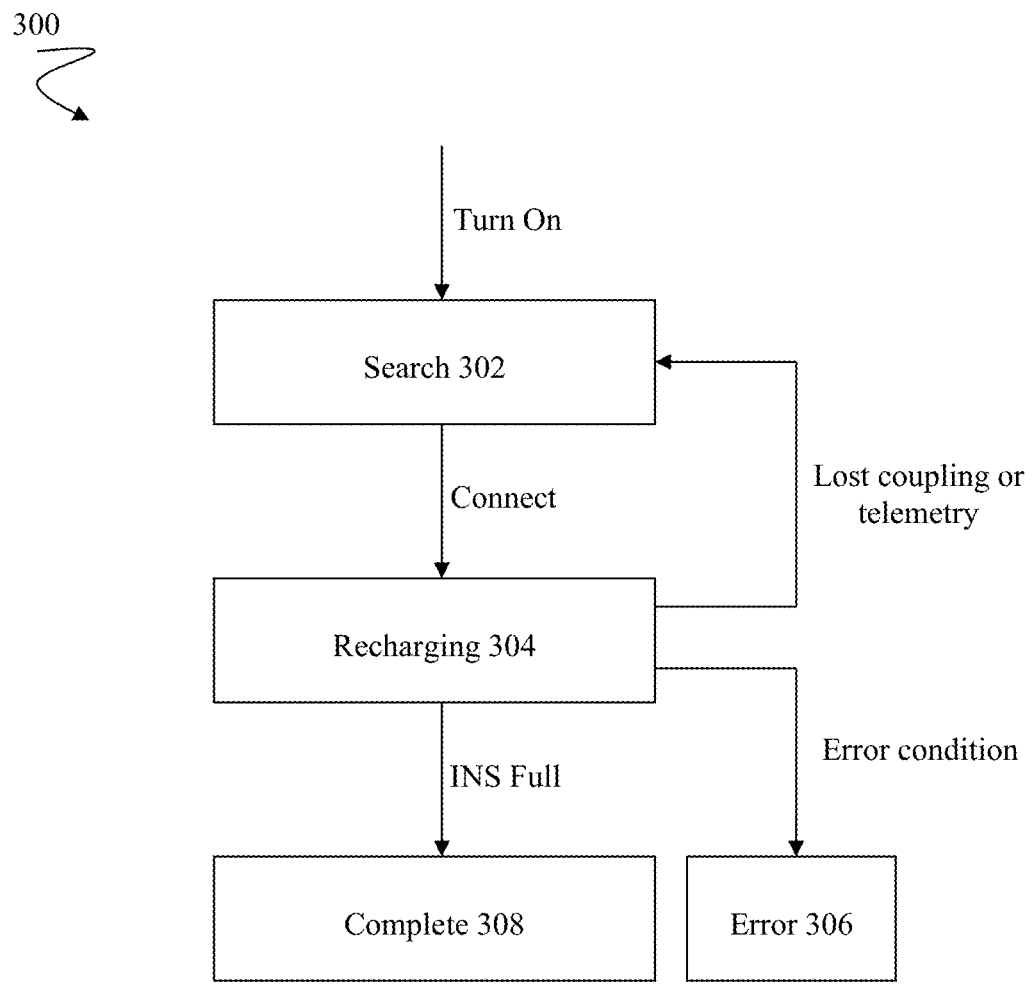
FIG. 3A is a state machine diagram for a method of presenting user interfaces during recharging of an implantable medical device, according to an embodiment.

Referring to FIG. 3A, a state machine 300 diagram for a method of presenting user interfaces during recharging of an implantable medical device is depicted, according to an embodiment. For example, state machine 300 can be implemented by recharger 104 or recharger 204.

In an embodiment, state machine 300 comprises three primary states: searching state 302, connected and recharging state 304, and error state 306. Complete state 308 is further depicted in FIG. 3A for clarity. Accordingly, the complex inner operation of an implantable medical device is reduced to a simple user interface model for patients.

Searching state 302 is a combination of all the modes that the patient can enter without doing a dock special button sequence, where the recharger is either attempting to detect metal or communicate with the implantable device. This can include various firmware states which all have various functionalities within the recharger and/or implantable medical device.

For example, in one firmware state, the recharger can attempt to detect the presence of metal by estimating the reflected impedance of the implantable device to allow for closed loop recharging. In another firmware state, the recharger can further check that the amount of metal present stays above the detection threshold so that if a user were to move the recharger over the implantable device somewhat quickly the recharger would not assume the implantable device is present. The output of this state indicates that metal loading is above the detection threshold and is stable. In an embodiment, the recharger alternates between states in which the recharger is attempting to communicate with the implantable device. Similarly, in another firmware state, the recharger is attempting to communicate with the implantable device after exiting metal loading detection. In another firmware state, the implantable device battery current (or charge efficiency, which is computed as power into the implantable device battery divided by power out of the recharge engine, referred to as tank power) drops below a threshold. In another firmware state, the telemetry connection is lost after closed loop connection. Searching state 302 can further comprise the failing or timing out of a telemetry session, in which the firmware can be in an open loop state (no feedback via telemetry from implantable device 202).

In searching state 302, radar-type (sequential spinning of 1-N LEDs) illuminated indications can be presented on the recharger interface button. In embodiments, a periodic beep can also be presented.

Recharging state 304 is a combination of all the modes of operation of the recharger where it is recharging an implantable device (e.g. closed loop and open loop). Accordingly, minor reconnections of the telemetry session or minor recharging states can be included in recharging state 304, as presented to the user.

In recharging state 304, a solid green indicator light can be presented when the implantable device has been found on the recharger interface button. Two tones, rising in pitch can also be presented. When the implantable device is recharging, a slow pulsing green indicator light can be presented on the recharger interface button. During recharging state 304, the recharger can specifically not inform the user when it is performing different functions of the algorithm (such as limiting power when a temperature limit has been reached, or when in constant-voltage charging mode of the implantable device 202). This information is not needed for the patient who simply needs to maintain the position of the recharger during this portion of operation.

Error state 306 corresponds to an error in the charging of the implantable medical device. In other embodiments, error state 306 can further correspond to an elective replacement indication. In some embodiments, an elective replacement indication can occur on the transition from 302 to 304, and specifically on the first transition from 302 to 304 (the initial connection) so as to not annoy the user.

In error state 306, a flashing amber indicator light can be presented on the recharger interface button. Two tones, falling in pitch and repeating can also be presented.

In operation, state machine 300 is entered by turning the recharger ON. Searching state 302 is then entered. In embodiments, state machine 300 can further comprise sleep or idle states in which the device appears inactive to the user. From sleep or idle, when the "power" button is pressed, state machine 300 enters searching state 302.

From searching state 302, in an embodiment, when the recharger is operably connected to the implantable medical device, state machine 300 moves to recharging state 304. For example, when below a metal coupling threshold value, state machine 300 has no confidence that an INS is present. When above the metal coupling threshold value, state machine 300 has reasonable confidence that an implantable device (of the appropriate size) is present.

In recharging state 304, the recharger recharges an implantable device. From recharging state 304, if the implantable medical device is successfully recharged (i.e. implantable device is full), state machine 300 can enter complete state 308. An appropriately-colored indicator light can be presented on the recharger interface button. In embodiments, a "complete" beep can also be presented.

From recharging state 304, if the recharger loses coupling or telemetry, state machine 300 returns to searching state 302. From connected and recharging state 304, if an unrecoverable error condition is encountered, state machine 300 enters error state 306.

Referring to FIG. 3B, a table of user interface indications for the state machine of FIG. 3A is depicted, according to an embodiment.

Figure 4:
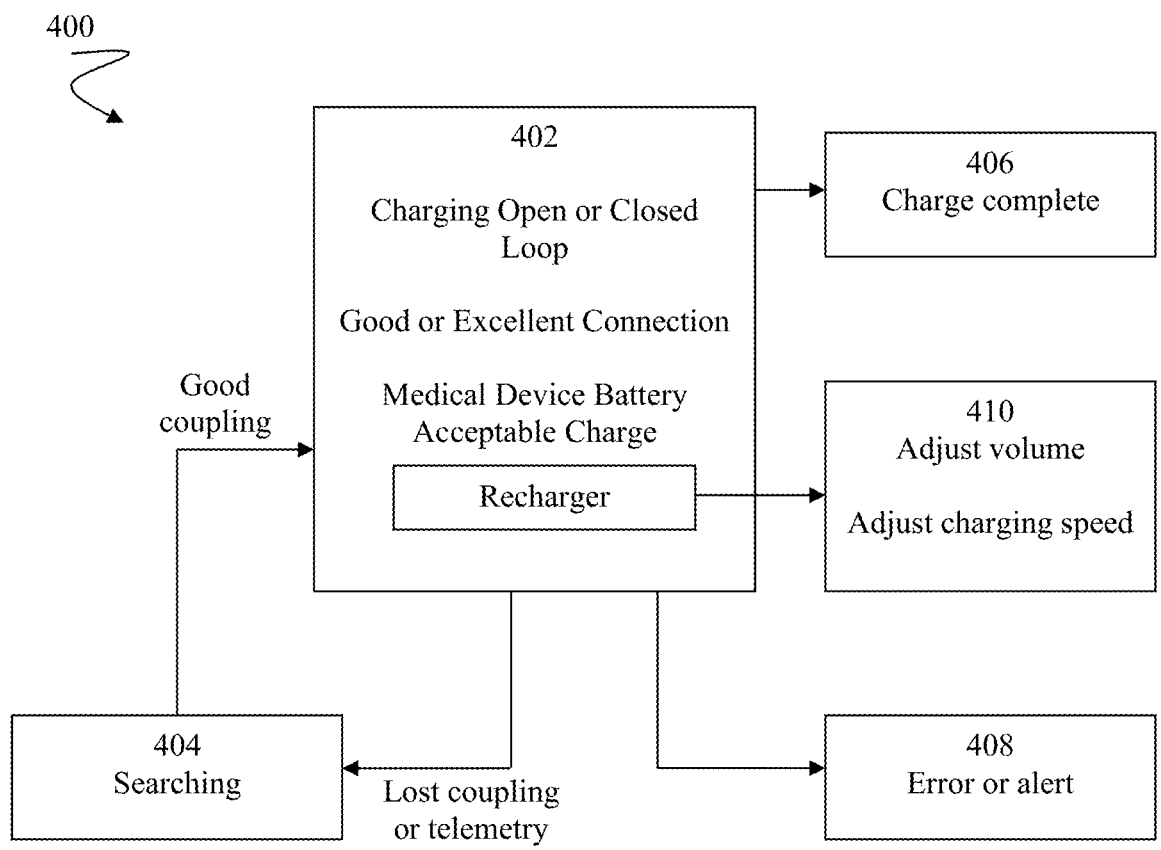
FIG. 4 is a state machine diagram for a method of presenting user interfaces on a client device during recharging of an implantable medical device, according to an embodiment.

Referring to FIG. 4, a state machine 400 diagram for a method of presenting user interfaces on a client device during recharging of an implantable medical device is depicted, according to an embodiment. For example, state machine 400 can be implemented by user device 106 or user device 206. As explained above, state machine 400 is intended to complement the light and sound indications on the recharger in a graphical form.

State machine 400 generally comprises four primary interfaces. A charging interface 402, a searching interface 404, a charge complete interface 406, and an error or alert interface 408. Accordingly, such states correspond to the states of the states of recharger interacting with the medical device.

Charging interface 402 comprises a graphical user interface presented on a user device when the recharger is charging the medical device in an open or closed loop, has a good or excellent connection with the medical device, and the medical device battery has an acceptable amount of charge. In an embodiment data communicated from a device, such as current and voltage can be utilized to compute charge efficiency and determine "good" and "excellent" in closed loop In embodiments, charging interface 402 can display different information in open loop and closed loop. In open loop, a number corresponding to the amount of metal loading can be displayed (and in which the user is instructed to make that number as large as possible).

Charging interface 402 on the GUI corresponds to a charging state of the recharger.

Searching interface 404 comprises a graphical user interface presented on a user device when the recharger has lost coupling or telemetry with the medical device. From searching interface 404, once the recharger has reestablished acceptable coupling, state machine 400 can proceed back to charging interface 402. Searching interface 404 on the GUI corresponds to a searching state of the recharger.

Charge complete interface 406 comprises a graphical user interface presented on a user device when the medical device is adequately charged. Charge complete interface 406 on the GUI corresponds to a complete state of the recharger.

Error or alert interface 408 comprises a graphical user interface presented on a user device when an error or alert is encountered for the medical device or recharger. Error or alert interface 408 corresponds to an error or alert (for example, elective replacement) state of the implantable device.

In an embodiment, from a graphical menu accessible in charging, closed loop interface 402, an additional adjustment interface 410 can be presented in which a user can adjust the volume of the recharger or the charging speed of the recharger. For example, if the user is experiencing discomfort, the speed of the recharge can be adjusted (e.g. reduced). In an embodiment, a speed value is stored persistently in the recharger, and can be updated via adjustment interface 410. In another embodiment, a maximum temperature value for the implantable device 202 or the recharger 204 can be adjusted via adjustment interface 410. Similarly, in other embodiments, adjustment interface 410 can be initiated via a menu and access to such settings can be restricted to clinicians only.

For example, FIGS. 5A-5F are screenshots of graphical user interfaces for a client device that complement a recharger, according to embodiments.

Figure 5A:
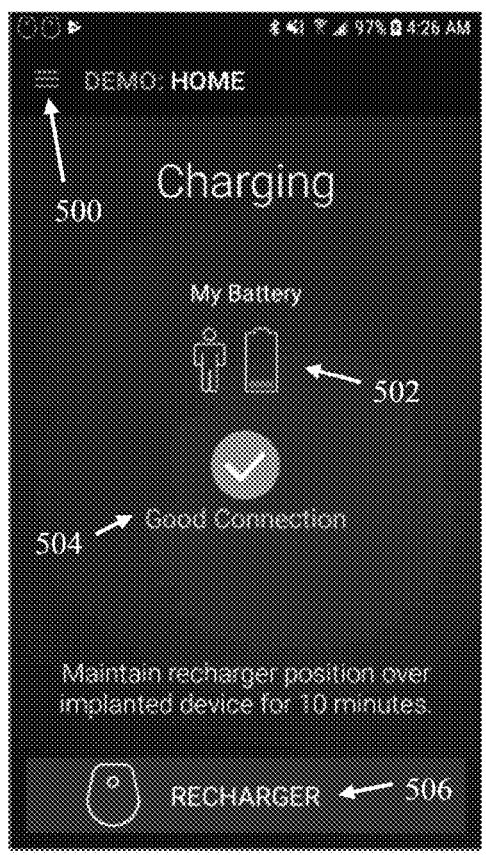
FIGS. 5A-5F are screenshots of graphical user interfaces for a client device that complement a recharger, according to embodiments.

FIG. 5A is a screenshot of a user interface for a client device in which the recharger is charging the medical device. The screenshot generally includes a menu button 500, a battery icon 502, a connection icon 504, and a recharger button 506. In an embodiment, FIG. 5A is presented when the recharger is in open loop charging the medical device and the coupling value is "good."

Figure 5B:
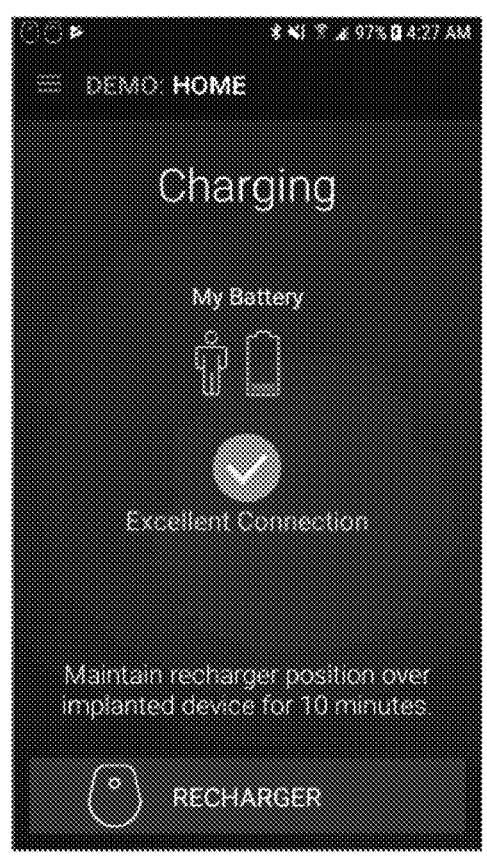
Figure 5C:
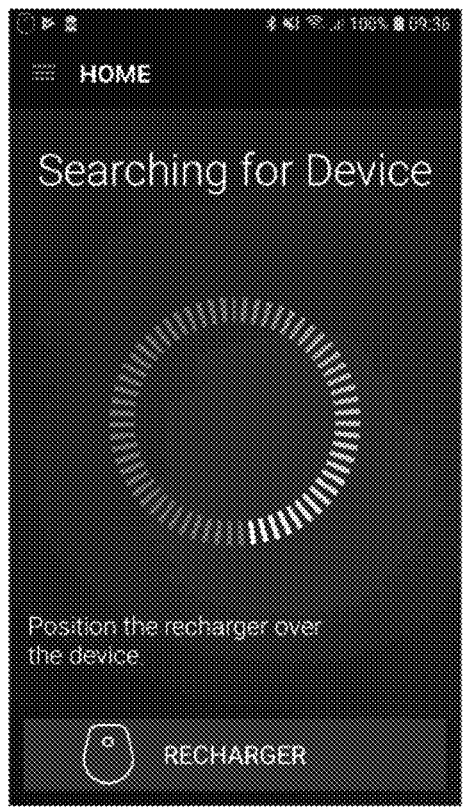
Figure 5D:
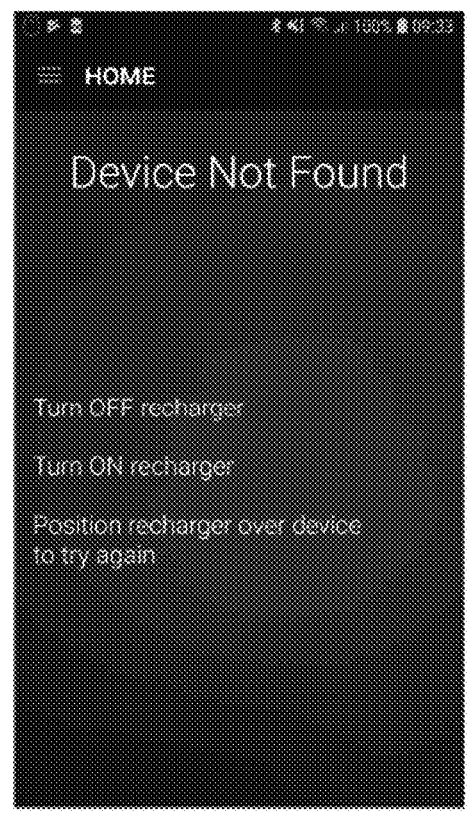
Figure 5E:
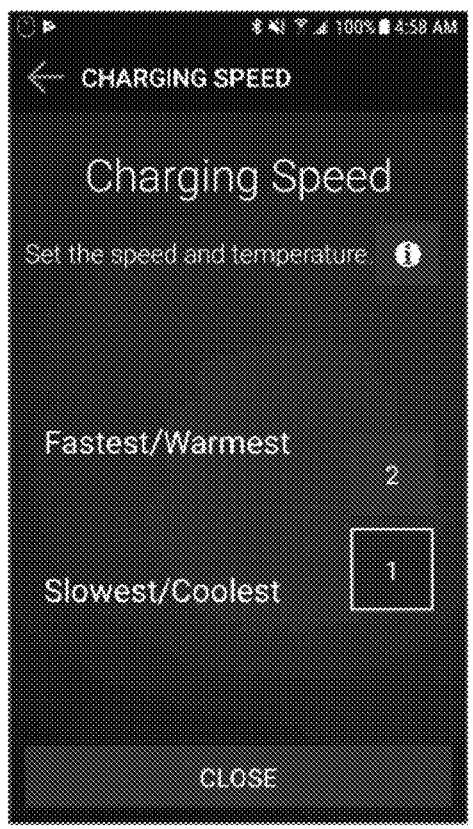

In an embodiment, a user can tap or activate menu button 500 to access charging speed settings and app information, such as in FIG. 5E. Battery icon 502 indicates the battery status. In an embodiment, a number next to battery icon 502 indicates the relative fullness of the battery (i.e. in percentage). In an embodiment, connection icon 504 indicates connection status between the recharger and the medical device. Finally, a user can tap or activate recharger button 506 to view recharger battery status and change the volume of the recharger.

FIG. 5B is a screenshot of a user interface for a client device in which the recharger is charging the medical device. In an embodiment, FIG. 5B is presented when the recharger is in open loop charging the medical device and the coupling value is "excellent." FIGS. 5A-5B can be presented in the state corresponding to charging interface 402.

FIG. 5C is a screenshot of a user interface for a client device in which the recharger is searching for the medical device to start a recharge session. FIG. 5C can be presented in the state corresponding to searching interface 404.

FIG. 5D is a screenshot of a user interface for a client device in which the recharger has experienced an error during recharging operation with the medical device. FIG. 5D can be presented in the state corresponding to error or alert interface 408.

FIG. 5E is a screenshot of a user interface for a client device in which the speed or temperature can be adjusted by the user. The charging speed interface of FIG. 5E allows the user to set the speed and warmth of the recharge session when the recharger is idle (both docked and undocked) and is locating or closed loop charging an INS. The fastest speed also creates the most warmth for the user and slowing the recharge will decrease the warmth. Pressing the values will cause the app to send the new recharge mode to the recharger. FIG. 5E can be presented in the state corresponding to adjustment interface 410.

Figure 5F:
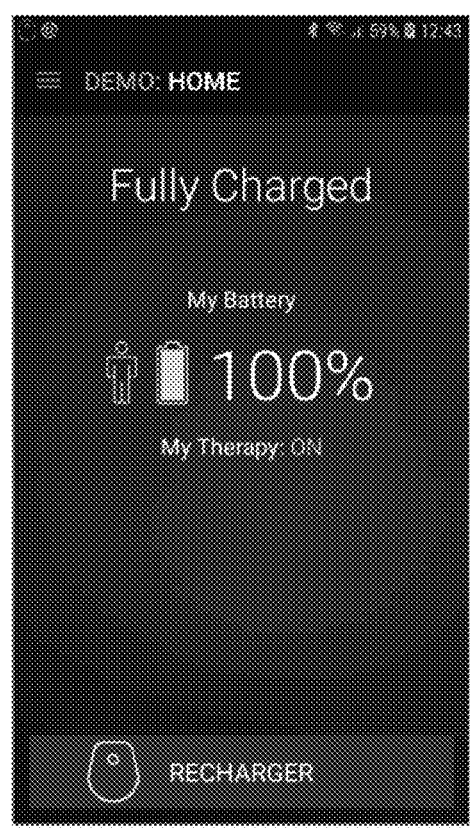

FIG. 5F is a screenshot of a user interface for a client device in which the recharger has completed charging the medical device. FIG. 5F can be presented in the state corresponding to chart complete interface 406.

Referring to FIG. 5G, an annotated table of graphical user interfaces and user instructions for a client device are depicted, according to an embodiment. During a searching state, a user can be instructed via the graphical user interface to either keep the recharger in place or move the recharger to attain a better connection.

For example, referring to the first row of FIG. 5G, a connection icon 550 can be displayed, indicating a good connection between the recharger and the medical device. A user is instructed to keep the recharger in place to maintain that connection until the battery of the implantable device reaches a level that it can respond to telemetry and the recharger can enter normal charging (closed loop).

Referring to the second row of FIG. 5G, an icon row 552 of three values, middle value 554, low value 556, and high value 558 can be displayed. The numbers depict relative metal loading (and thus the connection strength between the recharger and the medical device). In an embodiment, a user is instructed to move the recharger until middle value 554 is closer to high value 558 than low value 556. Once a relatively acceptable connection is made, the user is instructed to keep the recharger in place to maintain that connection until the battery of the medical device begins to charge.

Figure 5H:
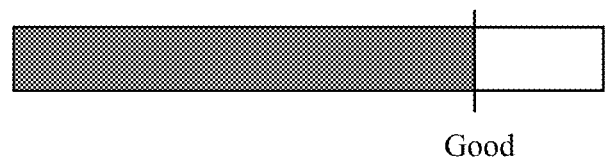
FIGS. 5H-5I are illustrations of graphical user interfaces for a client device, according to an embodiment.
Figure 5I:
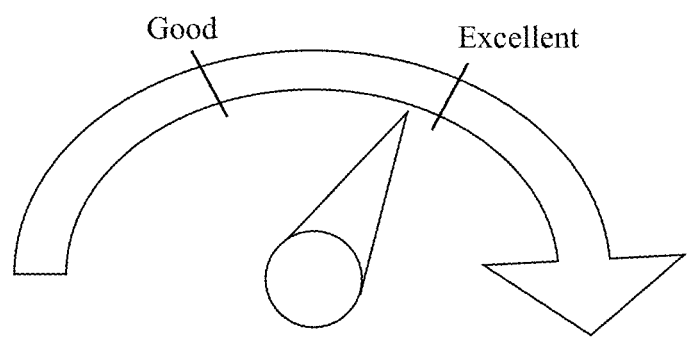

Referring further to FIGS. 5H-5I, additional connection indicators are considered. In an embodiment, a continuous bar 560 can be displayed, with a "good" indication when an acceptable connection is made and maintained. In another embodiment, a speedometer 562 can be displayed, with relative "good" to "excellent" indications. In embodiments, "good" or "excellent" can be arranged at fixed positions along the bar or indicator. Different colors can be displayed when the displayed value is above or below certain thresholds.

Accordingly, a "binary" display of good or bad is displayed, which further aids the user experience, as the user does not need to worry about relative degrees of good or bad. These relative degrees are handled internally by the UI engines in their intentional hiding of information.

In another embodiment, a connection indicator can display the estimated time remaining; for example, "Time to Full: 45 to 60 min," "45 to 60 min remaining," or "60 min" in a conservative estimate.

Figure 5J:
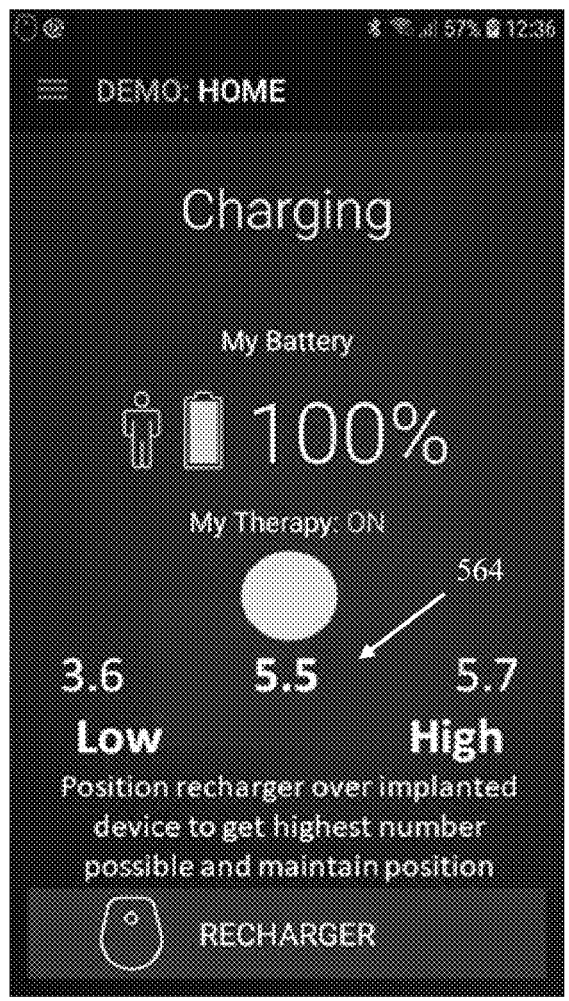
FIG. 5J is a screenshot of a graphical user interface for a client device, according to an embodiment.

Referring to FIG. 5J, a screenshot of a graphical user interface for a client device is depicted, according to an embodiment. In an embodiment, instead of a searching interface, a state indicating a connection in closed loop with poor coupling to the recharger can be displayed.

For example, a charge efficiency or INS battery current can be displayed at 564, rather than metal level. In an embodiment, a user can also utilize the screen of FIG. 5J to select a locate-mode feature, for example, from menu button 500 as illustrated in FIG. 5A. In embodiments, with respect to searching or locating, an audible tone can be presented and adjusted in frequency or pitch to correspond to the amount of metal detected. In an embodiment, an audible tone can likewise be presented based on charge efficiency or INS battery current.

Figure 6:
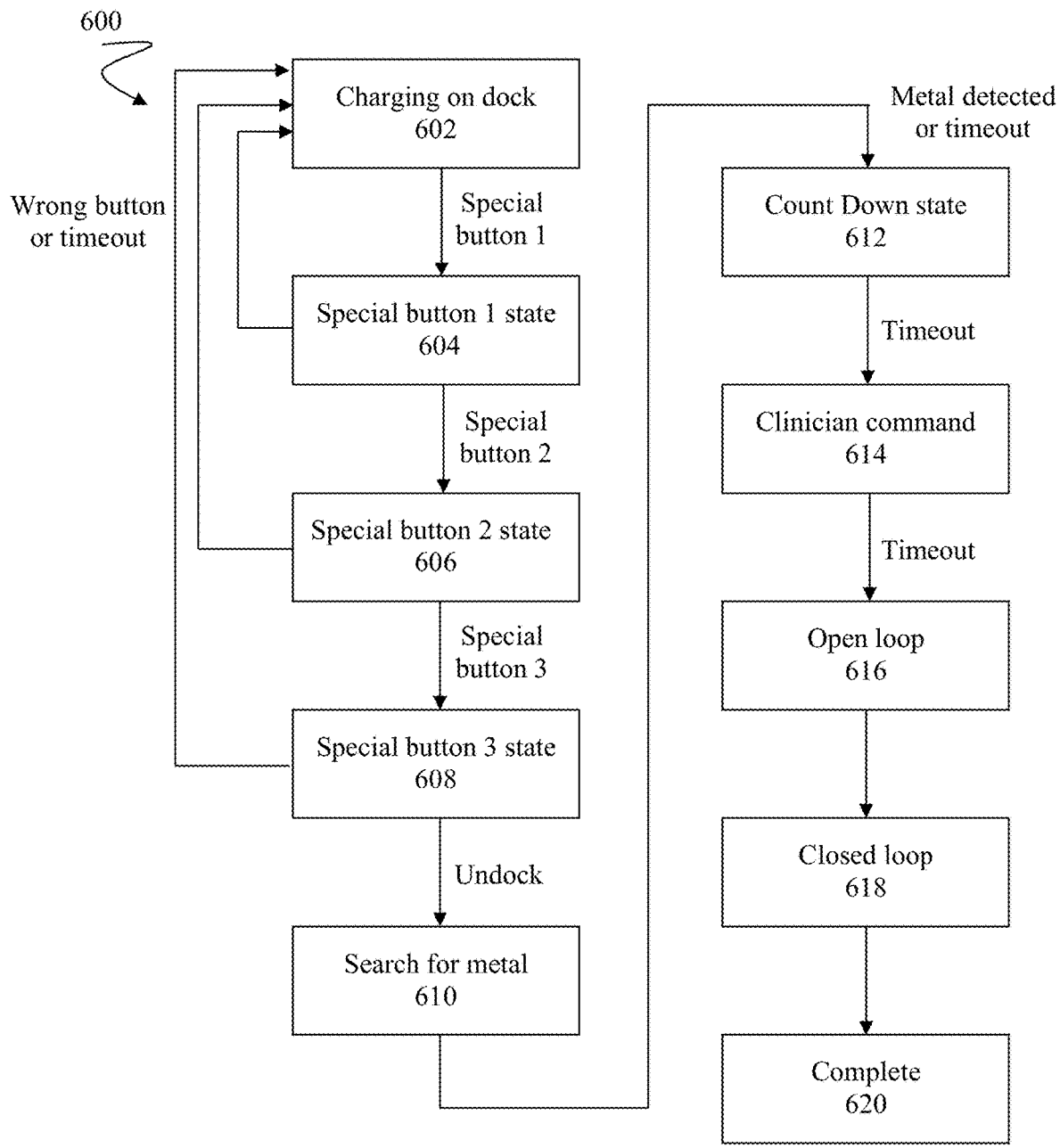
FIG. 6 is a flowchart of a method of special mode operation for recharging of an implantable medical device, according to an embodiment.

Referring to FIG. 6, a flowchart of a method 600 of special mode operation for recharging of an implantable medical device is depicted, according to an embodiment.

For example, method 600 can activate a clinician mode on the recharger, which can be activated with a unique sequence of button presses (and with a conditional hardware state, such as being connected to a charging dock). In embodiments of the recharger having only a single button, this functionality is achieved by method 600. Further, it is worth noting the clinician mode is initiated without user device application software (i.e. on user device 106 or 206).

At 602, the recharger is operably coupled to a dock. For example, the recharger can be operably coupled via USB or AC power. This further hardware coupling provides additional security against a user accidentally entering the special clinician mode.

From 602, a special button 1 press can be made by the clinician user. For example, special button 1 can be pressed for a duration of between 0.25 and 3.0 seconds. At 604, special button 1 state then is entered.

From 604, a special button 2 press can be made by the clinician user. For example, special button 2 can be pressed for a duration of between 0.25 and 3.0 seconds. At 606, special button 2 state is then entered.

From 606, a special button 3 press can be made by the clinician user. For example, special button 3 can be pressed for a duration of between 3.0 and 7.0 seconds. At 608, special button 3 state is then entered.

Other sequences and durations are, of course, possible. However, such a sequence as described in method 600 maximizes usability and minimizes the likelihood that a patient accidentally enters the sequence.

States 602, 604, and 606 are shown as separate for ease of explanation. However, states 602, 604, and 606 can be combined, as will be readily understood by one of skill in the art.

Figure 7A:
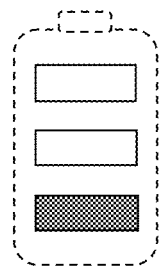
FIGS. 7A-7C are illustrations of user interfaces during special mode operation for recharging of an implantable medical device, according to an embodiment.
Figure 7B:
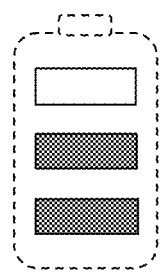
Figure 7C:
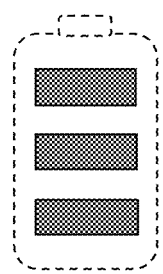

Referring also to FIGS. 7A-7C, illustrations of user interfaces during special mode operation for recharging of an implantable medical device are depicted, according to an embodiment. For example, upon entering special button 1 state, a battery indicator light can be depicted with one single bar illuminated, as in FIG. 7A. Upon entering special button 2 state, the battery indicator light can be depicted with two bars illuminated, as in FIG. 7B. Upon entering special button 3 state, the battery indicator light can be depicted with three bars illuminated, as in FIG. 7C. In an embodiment, the battery indicator light can be displayed in a different color (e.g. amber) than normal operation (e.g. green). These visual markers provide the clinician user an indication he is correctly entering the required sequence.

Referring again to FIG. 6, from 608, the recharger is then uncoupled from the dock. At 610, recharger conducts a search for metal to detect an INS.

From 610, the recharger can detect metal and enter a countdown state at 612. In embodiments, from 610, the recharger can also time out and enter the countdown state at 612.

In the countdown state at 612, in an embodiment, the recharger can emit a countdown tone such that something imminent is about occur. For example, the tone can be faster than the aforementioned searching state and last for 10 seconds. Other frequencies and durations are considered.

From 612, a timeout is determined and the clinician-only command is transmitted from the recharger to the INS at 614. The clinician-only command is intended to be used only by clinicians, as it can be a hardware reset, firmware reset, or other critical command.

From 614, a further timeout is determined and open loop operation of the recharger is conducted at 616. In an embodiment, States 610, 612, 614, and 616, can be displayed on the UI (power button indicator or battery indicator) in a different color than normal operation to indicate clinician-only operation.

At 618, normal closed loop operation of the recharger is conducted.

Finally, at 620, special mode operation is complete.

Other types of special mode operation are, of course, considered, in addition to or to supplement the recharge of method 600, such as hardware or setting resets, sustained operation in a particular mode, and so on.

Figure 8A:
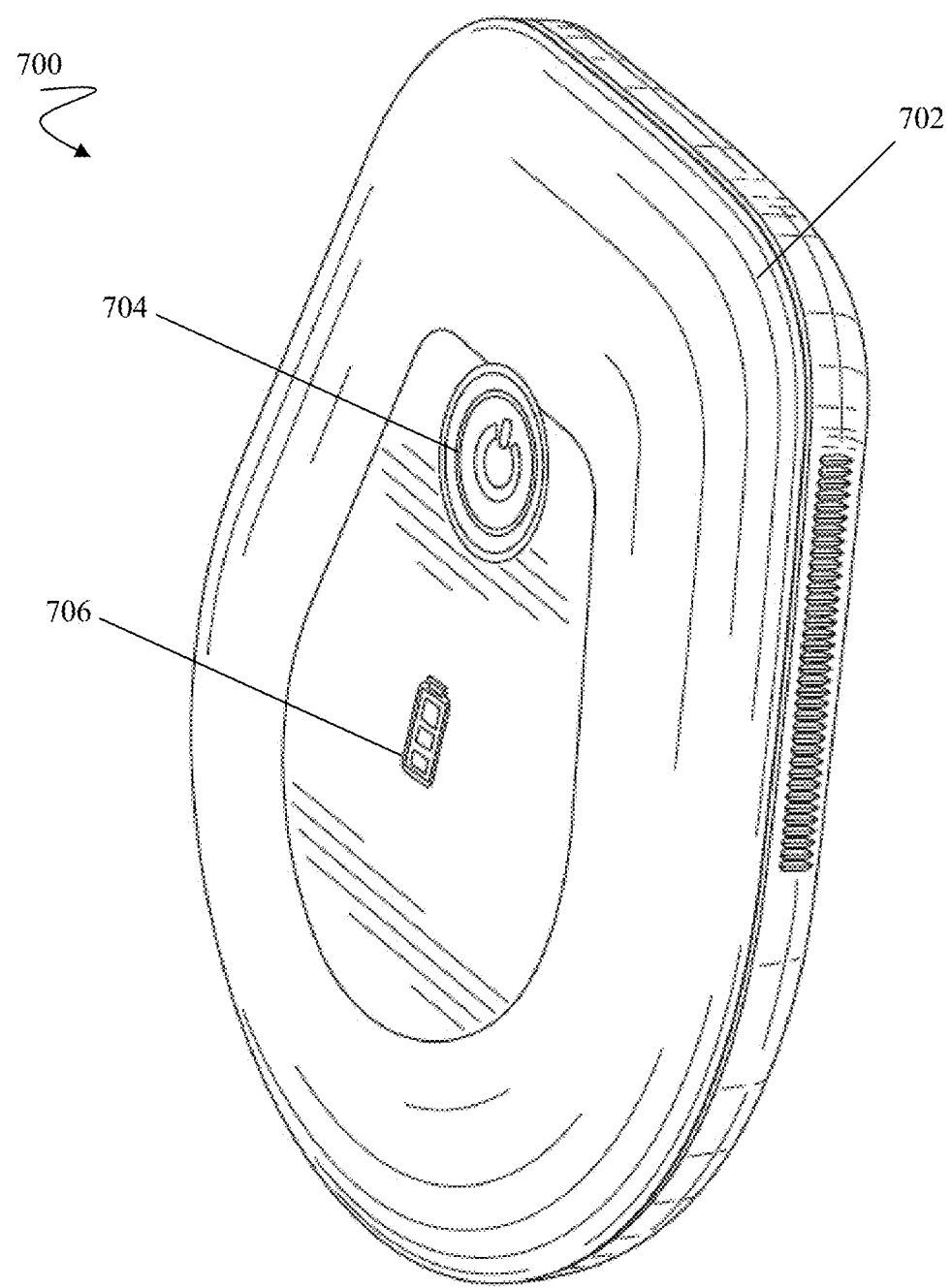
FIG. 8A is a perspective view of a recharger for an implantable medical device, according to an embodiment.

Referring to FIG. 8A, a perspective view of a recharger 700 for an implantable medical device is depicted, according to an embodiment. Recharger 700 generally comprises a housing 702, a single power button 704, and a battery indicator 706. For example, single power button 704 can correspond to the power button illumination described with respect to FIGS. 3A and 3B. In an embodiment, a ring of LEDs can be disposed around or under power button LED 704 such that "rotational" displays can be created by illuminating subsequent LEDs. Battery indicator 706 can correspond to the battery indicator light illumination described in FIG. 6.

Figure 8B:
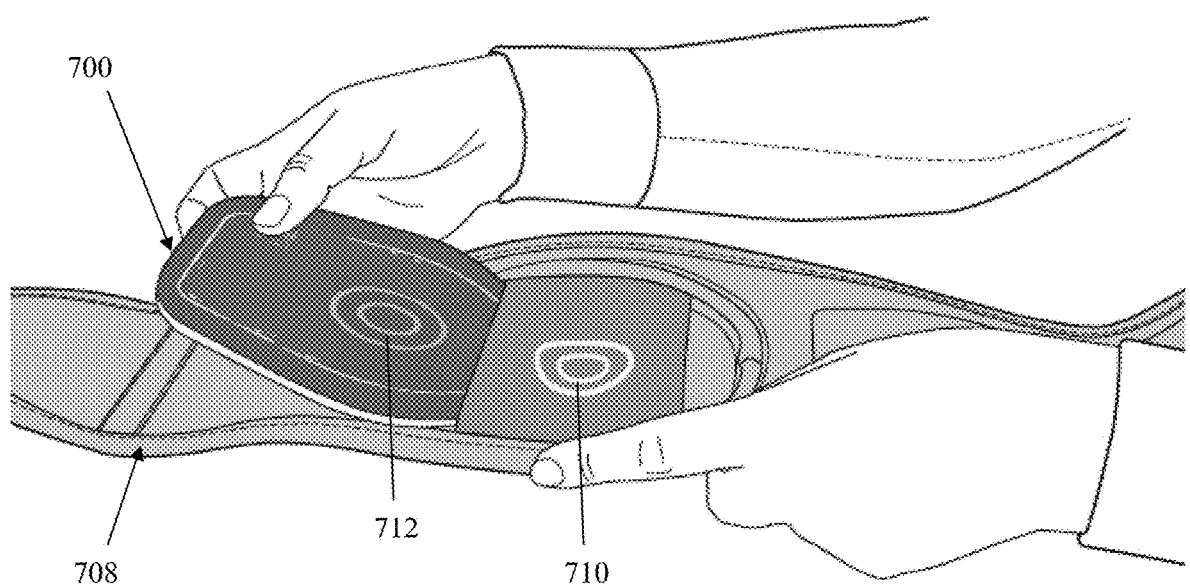
FIG. 8B is a perspective view of a recharger for an implantable medical device with a fixation element, according to an embodiment.

Referring to FIG. 8B, a perspective view of recharger 700 for an implantable medical device with a fixation element 708 is depicted, according to an embodiment. In an embodiment, recharger 700 further comprises patient-facing UI in the context of a target symbol to integrate recharger 700 and fixation element 708.

For example, fixation element 708 can comprise a belt, drape, or other coupling element (such as adhesive pads, etc.) configured to fasten or hold recharger 700 at a particular position on the patient. Accordingly, fixation element 708 can comprise coupling element target symbol 710 as a guide for placement of recharger 700 over the implantable device.

In an embodiment, recharger 700 further comprises recharger target symbol 712 on the side of recharger 700 opposite from single power button 704 and battery indicator 706. Coupling element target symbol 710 and recharger target symbol 712 can be the same, or different, in embodiments (depicted in FIG. 8B as the same).

In operation, a patient user can couple recharger 700 with fixation element 708 by lining up recharger target symbol 712 and coupling element target symbol 710. As depicted in FIG. 8B, recharger 700 is slid into a pocket of fixation element 708 to align recharger target symbol 712 and coupling element target symbol 710. By properly aligning recharger 700 with fixation element 708, a known and adequate placement of the telemetry components of recharger 700 is achieved. Once recharger 700 is secured in fixation element 708, coupling element target symbol 710 can be centered by the user over the implantable device after palpating the implantable device. In general, little or no further adjustment is needed when an implantable device is within the target, thereby simplifying the task of charging the implantable device.

Figure 9A:
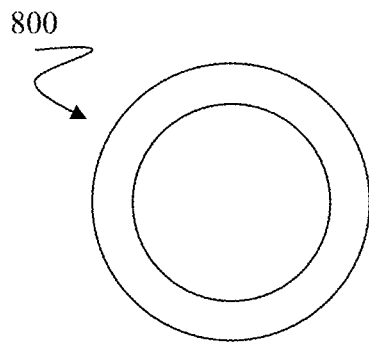
FIGS. 9A-9D are illustrations of user interfaces for a recharger for an implantable medical device, according to an embodiment.
Figure 9B:
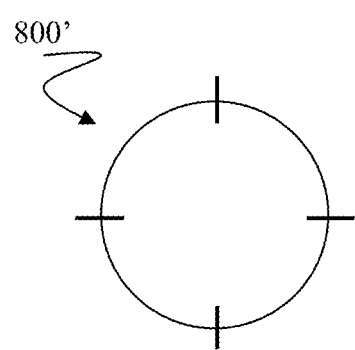
Figure 9C:
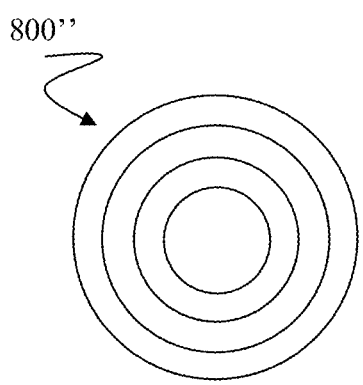
Figure 9D:
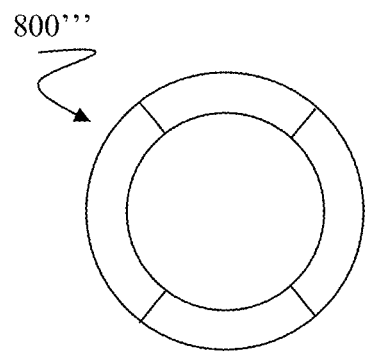

Referring also to FIGS. 9A-9D, illustrations of user interfaces for a recharger for an implantable medical device is depicted, according to an embodiment. In particular, and as depicted in FIG. 9A, target symbol 800 can be two concentric circles. Two concentric circles communicate optimal position. Referring to FIG. 9B, target symbol 800' can be crosshairs. Referring to FIG. 9C, target symbol 800" can be multiple concentric circles. Referring to FIG. 9D, target symbol 800''' can be two concentric circles divided into quarters. In embodiments, the relative outer circle diameters are intentionally smaller than an "excellent" coupling area so patients attempt to locate with enhanced precision.

Embodiments of the present disclosure may be used with a variety of implantable medical devices, including but not limited to nerve stimulation devices (also known as neuro stimulators or neuromodulation devices), drug delivery pumps, cardiac pacemakers, defibrillators, or implantable cardioverter-defibrillators. In embodiments, neuromodulation devices may be used to stimulate a variety of nerves or associated tissues for treating a variety of conditions. Electrical stimulation may be delivered for spinal cord stimulation (SCS), peripheral nerve stimulation (PNS), peripheral nerve field stimulation (PNFS), deep brain stimulation (DBS), cortical stimulation (CS), pelvic floor stimulation, sacral nerve stimulation, tibial nerve stimulation, gastric stimulation, and the like.

In an example, embodiments of the present disclosure may be used as part of a system for treating pelvic health conditions including incontinence, overactive bladder, pelvic pain or other pelvic floor disorders. Referring to FIGS.

Figure 10A:
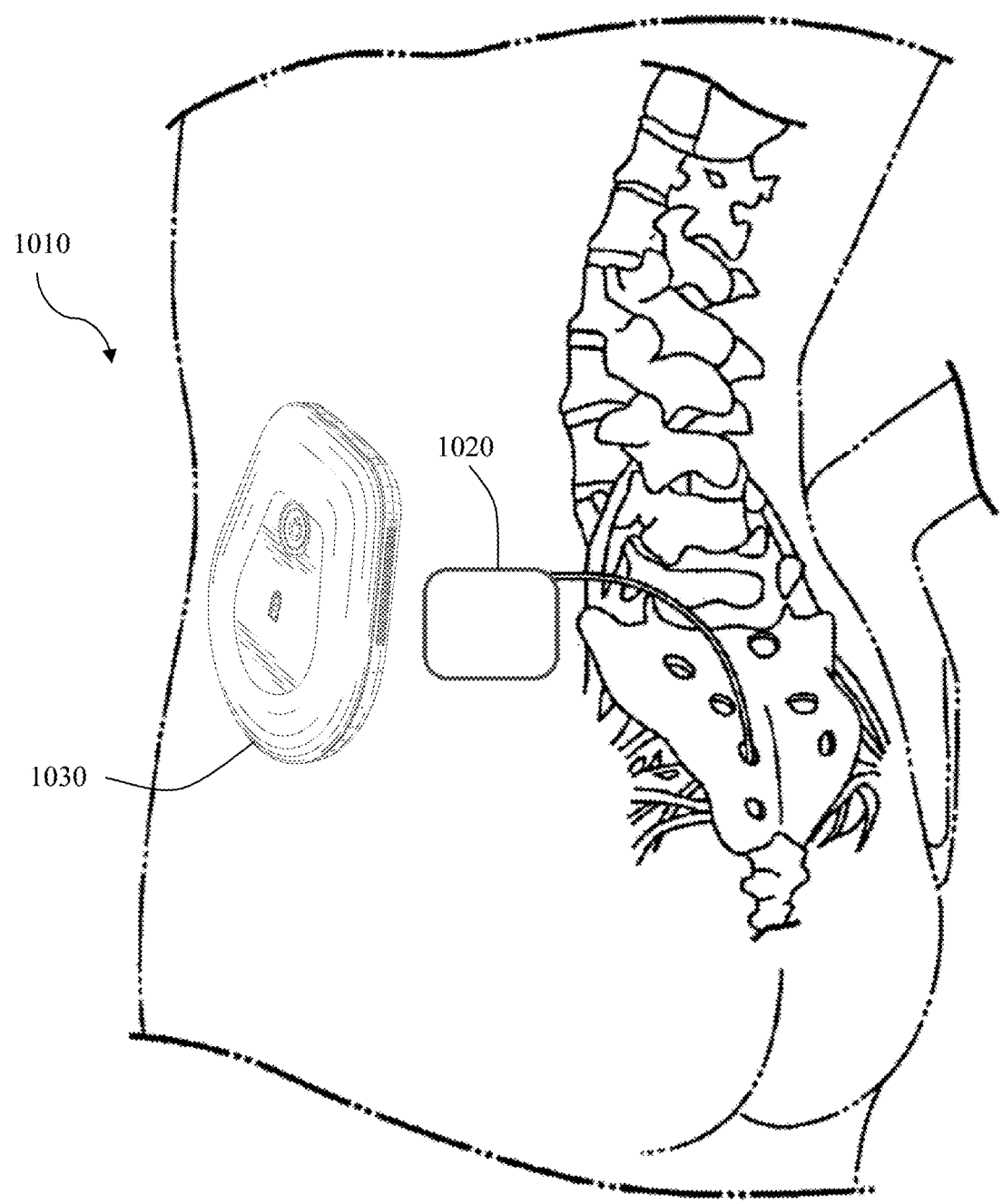
FIG. 10A is a schematic of a sacral nerve stimulation system according to an embodiment.
Figure 10B:
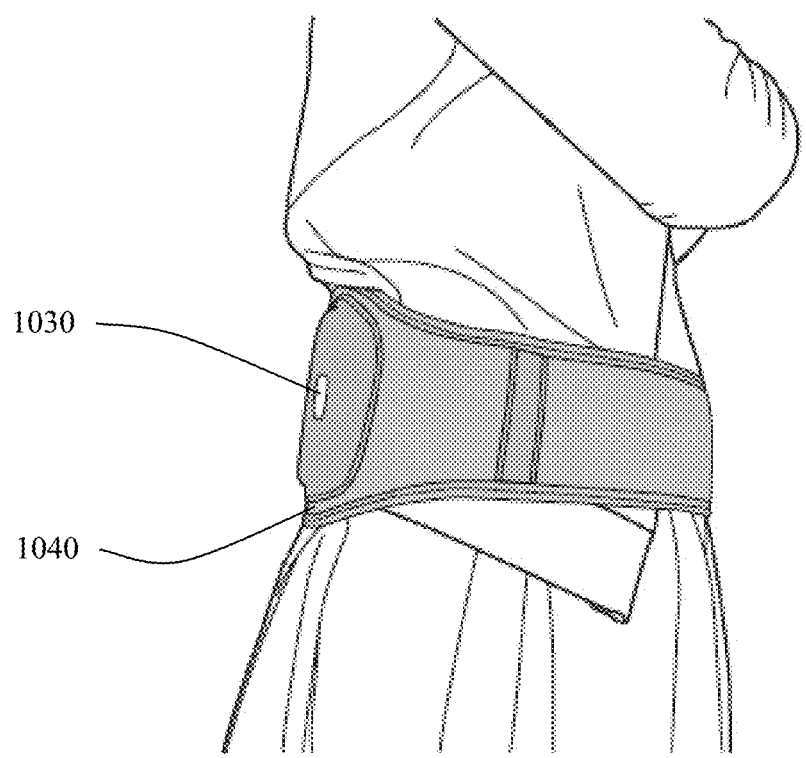
FIG. 10B is a schematic of a sacral nerve stimulation system with a wearable belt according to an embodiment.

10A-B, embodiments of the present disclosure can be implemented as part of a sacral nerve stimulation system 1010, including a rechargeable implantable nerve stimulation device 1020 and an external recharger 1030, wherein external recharger 1030 can be positioned on or proximate to skin of the patient over the location of implantable nerve stimulation device 1020 to facilitate recharging. Referring to FIG. 10B, external recharger 1030 may also be wearable on the patient such as with a belt 1040.

Figure 11:
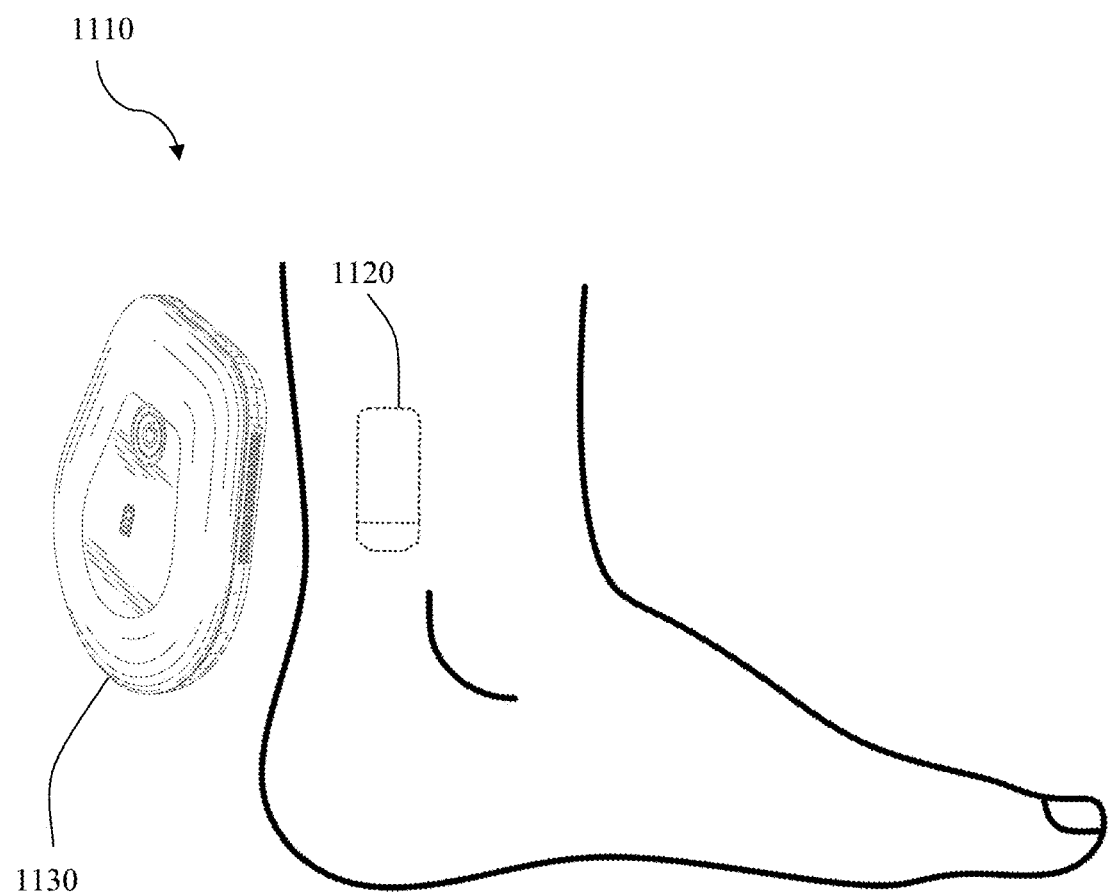
FIG. 11 is a schematic of a tibial nerve stimulation system according to an embodiment.

Referring to FIG. 11, in another example pertaining to treatment of pelvic health disorders, embodiments of the present disclosure may be implemented as part of a tibial nerve stimulation system 1100, including an implantable tibial nerve stimulation device 1120 and an external recharger 1130, wherein external recharger 1130 can be positioned on or proximate to skin of the patient over the location of implantable nerve stimulation device 1120 to facilitate recharging. Tibial nerve stimulation system 1110 may also include a wearable ankle cuff to hold external recharger 1130 in position on an ankle of a patient.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Various embodiments of systems, devices, and methods have been described herein. These embodiments are given only by way of example and are not intended to limit the scope of the claimed embodiments. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed embodiments.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

What is claimed is:

1. An external charging device for providing power to a rechargeable implantable device, the external charging device comprising:
    a housing;
    a single button arranged in the housing;
    an indicator light illuminating the single button, the indicator light comprising at least one light emitting diode (LED);
    at least one processor and a memory operably coupled to the at least one processor; and
    instructions that, when executed on the at least one processor, cause the at least one processor to:
        determine a primary firmware state of the external charging device during recharging of the rechargeable implantable device, wherein the primary firmware state is indicative of different operations of the external charging device and each of the different operations including a plurality of various, aggregated firmware states of various functionalities associated with that primary firmware state,
        display a searching indication using the indicator light when the primary firmware state is determined to be in a searching state,
        display a charging indication using the indicator light when the primary firmware state is determined to be a charging state, and display an error indication using the indicator light when the primary firmware state is determined to be an error state.

2. The external charging device of claim 1, wherein the searching indication and the charging indication are in a first color and the error indication is in a second color, the first color being different than the second color.

3. The external charging device of claim 1, wherein the searching state includes at least two firmware states.

4. The external charging device of claim 3, wherein the at least two firmware states include the external charging device attempting to detect metal and the external charging device attempting to communicate with the rechargeable implantable device.

5. The external charging device of claim 1, wherein the charging state includes at least two firmware states.

6. The external charging device of claim 5, wherein the at least two firmware states include open loop charging and closed loop charging.

7. The external charging device of claim 1, further comprising an alignment indicator arranged on the housing.

8. The external charging device of claim 7, wherein the alignment indicator comprises two concentric circles to be positioned relative to a patient user coupling alignment indicator.

9. A system for medical treatment, the system comprising:
a rechargeable implantable medical device configured to provide a medical therapy to a patient; and
a recharger including
an indicator light having a at least one light emitting diode (LED) illuminating a single button,
at least one processor and a memory operably coupled to the at least one processor; and
instructions that, when executed on the at least one processor, cause the at least one processor to implement:
a user interface engine configured to determine a primary firmware state of an external charging device during recharging of the rechargeable implantable device, wherein the primary firmware state is indicative of different operations of the external device and each of the different operations including a plurality of various, aggregated firmware states of various functionalities associated with that primary firmware state, and
display status of the recharging on the indicator light based on the determined primary firmware state.

10. The system of claim 9, wherein the rechargeable implantable medical device is an implantable neurostimulator (INS).

11. The system of claim 10, wherein the primary firmware state includes a searching state corresponding to the external charging device attempting to detect metal on the INS or the external charging device attempting to communicate with the INS.

12. The system of claim 10, wherein the primary firmware state includes a charging state corresponding to open loop charging of the INS closed loop charging of the INS.

13. The system of claim 9, wherein the primary firmware state includes a plurality of charging-related states and the indicator light is a binary indication of charging or not charging.

14. The system of claim 9, wherein the primary firmware state includes a plurality of searching-related states and the indicator light is a binary indication of searching or not searching.

15. The system of claim 9, further comprising:
a mobile user device including computing hardware of at least one processor and memory operably coupled to the at least one processor; and
instructions that, when executed on the mobile user device, cause the mobile user device to implement:
an input/output engine operably coupled to the recharger and configured to transmit data to and receive data from the recharger;
a graphical user interface engine configured to display interfaces according to a state machine including:
a graphical indication of charging when the recharger is actively charging the rechargeable implantable medical device,
a graphical indication of searching when the recharger is actively searching for the rechargeable implantable medical device, and
a graphical indication of an error when the recharger cannot charge or find the rechargeable implantable medical device.

16. The system of claim 15, wherein the graphical indication of searching includes a row of three values corresponding to the level of metal loading between the recharger and the rechargeable implantable medical device.

17. The system of claim 16, wherein the three values includes a low value, a high value, and an actual value.

* * * * *